United States Patent [19]

Jani et al.

[11] Patent Number: 4,911,920

[45] Date of Patent: Mar. 27, 1990

[54] SUSTAINED RELEASE, COMFORT FORMULATION FOR GLAUCOMA THERAPY

[75] Inventors: Rajni Jani; Robert G. Harris, both of Fort Worth, Tex.

[73] Assignee: Alcon Laboratories, Inc., Fort Worth, Tex.

[21] Appl. No.: 154,514

[22] Filed: Feb. 5, 1988

Related U.S. Application Data

[63] Continuation of Ser. No. 890,519, Jul. 30, 1986, abandoned, which is a continuation of Ser. No. 667,003, Oct. 31, 1984, abandoned.

[51] Int. Cl.⁴ ............................................. A61K 31/78
[52] U.S. Cl. ...................................... 424/78; 424/81; 514/913
[58] Field of Search .................... 514/913; 424/19, 78, 424/81

[56] References Cited

U.S. PATENT DOCUMENTS

| | | | |
|---|---|---|---|
| 3,867,519 | 2/1975 | Michaels | 424/19 |
| 3,962,414 | 6/1976 | Michaels | 424/19 |
| 3,987,163 | 10/1976 | Rankin | 424/78 |
| 4,127,674 | 11/1978 | Leopold | 424/324 |
| 4,207,890 | 6/1980 | Mamajek et al | 128/223 |
| 4,271,143 | 6/1981 | Schoenwald et al. | 424/78 |
| 4,407,792 | 10/1983 | Schoenwald et al. | 424/81 |
| 4,462,982 | 7/1984 | Samejima et al. | 429/19 |
| 4,521,414 | 6/1985 | Chion et al. | 514/229 |

OTHER PUBLICATIONS

Chem. Abst. 98:210936j (1983) Heath et al.

*Primary Examiner*—Shep K. Rose
*Assistant Examiner*—Zohyeh A. Fay
*Attorney, Agent, or Firm*—James A. Arno; Gregg C. Brown; Sally Yeager

[57] ABSTRACT

Disclosed are nonstinging, sustained release ophthalmic formulations to control intraocular pressure in antiglaucoma therapy comprising a basic active, a cation exchange resin, and, inter alia, an acidic, mucomimetic polymer. Also disclosed are methods of treatment comprising administering such formulations topically to the eye when indicated for control and lowering of intraocular pressure.

12 Claims, No Drawings

SUSTAINED RELEASE, COMFORT FORMULATION FOR GLAUCOMA THERAPY

This is a continuation, of application Ser. No. 890,519 which is a continuation of application Ser. No. 667,003 both abandoned.

BACKGROUND OF THE INVENTION

This invention relates to ophthalmic formulations useful in controlling and lowering intraocular pressure (IOP) in the treatment of glaucoma. The formulations of the present invention are characterized as long lasting (sustained release) and are initially and continually comfortable to the eye. Specifically, the invention relates to formulations of the above characteristics which comprise, inter alia, a basic active and a cationic exchange resin (finely divided) dispersed in an aqueous solution or gel of an acidic, mucomimetic polymer. Such resulting aqueous gel or pourable liquid formulations are characterized by controlled cationic-anionic interactions, which appear to be responsible for the resulting comfort and sustained release properties. This invention also relates to methods of treatment which comprise administering the described compositions when indicated for treating ocular hypertension and glaucoma.

The term "basic active" means the active ingredient or ingredients in the disclosed formulations which have the desired effect on intraocular pressure and which bear, or are capable of bearing, a positive charge during formulation of the final product or as formulated in the final product form. Thus, the term basic, or cationic, active is descriptive for purposes of the disclosure and claims.

Such basic actives include all presently known beta blockers which demonstrate the requisite cationic charge and IOP effect. Typically, such beta blockers are represented by the following generic structure, which structure also represents the beta blocker basic actives of the present disclosure:

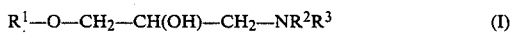

$$R^1\text{—O—}CH_2\text{—}CH(OH)\text{—}CH_2\text{—}NR^2R^3 \qquad (I)$$

wherein:
  $R^1$ is a substituted or unsubstituted cyclic or aliphatic moiety; cyclic moieties include mono- and polycyclic structures which may contain one or more heteroatoms selected from C, N, and O; $R^2$ and $R^3$ are independently selected from H and substituted and unsubstituted alkyl. With regard to Structure (I), above, the following references are incorporated herein by reference: *Annular Reports in Medicinal Chemistry* 14, 81–87 (1979); *J. Med. Chem.* 1983, 26, 1570–1576; *ibid.*, 1984, 27, 503–509; *ibid.*, 1983, 26, 7–11; *ibid.*, 1983, 26, 1561–1569; *ibid.*, 1983, 1109–1112; *ibid.*, 1983, 26, 950–957; *ibid.*, 1983, 26, 649–657; and *ibid.*, 1983, 26, 352–357. Representative such basic actives are: betaxolol, timolol, befunolol, labetalol, propanolol, bupranolol, metaprolol, bunalol, esmalol, pindolol, carteolol, hepunolol, metipranolol, celiprolol, azotinolol (S-596), diacetolol, acebutolol, salbutamol, atenulol, isoxaprolol, and the like.

The definition of basic active also includes the following classes of drugs which are used in treatment of ocular hypertension and glaucoma: pilocarpine; epiniphrine; proepinephrine; norepinephrine; pronorepiniphrine; clonidine; and clonidine derivatives, for example, p-aminoclonidine and p-acetoamidoclonidine.

Thus, in summary, the basic active component of the present invention is defined by its intraocular pressure lowering effect or static control thereof, and by its cationic nature in an aqueous medium in the pH range of from 3.0 to 8.5. The following patent publications, which are incorporated herein by reference, further representatively demonstrate the basic actives of the present invention: U.S. Pat. Nos. 4,252,984; 3,309,406; 3,619,370; 3,655,663; 3,657,237; 4,012,444; 3,663,607; 3,836,671; 3,857,952; 3,202,660; and 2,774,789.

DETAILED DESCRIPTION OF THE INVENTION

The ophthalmic formulations of the present invention are in the form of: anhydrous salts; pourable, aqueous dispersions; and aqueous gels. The formulations comprise, in addition to conventional ingredients which provide, for example, bacteriostatic and formulatory balance functions, a critical polyanionic polymer, a cation exchange resin and the basic active of choice. Such anhydrous salt forms are incorporated into ointments or solid ocular inserts which form colloidal gels in situ on administration to the eye. The pourable liquid and gel embodiments are applied topically to the eye. It should be noted that such liquid and gel embodiments can be obtained from the anhydrous form on formulation with water.

The formulations of the present invention demonstrate sustained release of the basic active and are comfortable on topical administration to the eye. It should be noted, in general sense, that a stinging sensation results when the basic actives, identified above, are administered neat. Thus, achieving both comfort and sustained release in an unexpected result and permits administration of a class of compounds that otherwise might not be considered.

Polyanionic Polymer Component

The high molecular weight, polyanionic polymers useful in the present invention have a molecular weight of from about 50,000 to about 6 million. The polymers are characterized as having carboxylic acid functional groups, and preferably contain from 2 to 7 carbon atoms per functional group. The gels which form during the preparation of the ophthalmic polymer dispersion have a viscosity of from about 1,000 to about 300,000 cps. In addition to the basic active-polymer (anioniccationic) interactions, mentioned above, the high molecular weight polymers used in the compositions of the present invention thicken the compositions to provide a gel, and provide a special type of rheology, i.e., plastic viscosity, which is translatable to the sustained release and comfort of the final compositions. Such compositions range in pH from 3.0 to 8.5.

The pourable liquid embodiments (administered as drops to the eye) of the present invention have a viscosity of from about 1 to 20,000 cps. The pH requirements are the same as recited above for the gel final products, i.e., pH 3.0–8.5.

The third pharmaceutical form of the present invention, the anhydrous salt form, is derived from a salt of the polycarboxylic acid polymer and the basic active. (The presence of the cationic ion exchange resin also contributes to salt formation; the nature of the ion exchange resin, in all embodiments of the present invention is defined below.) Such salts can be formulated, or reconstituted, to aqueous gels and pourable dispersions, as described above, on addition of water; or can be formulated as ocular inserts according to known technology and shapes; or they can be combined with an oleaginous vehicle to form an ophthalmic ointment. All such final ophthalmic pharmaceutical forms are fully described below.

The term "plastic viscosity", above, is indicative of a material that does not perceptibly flow until a certain force or stress value is exceeded; this force or stress is referred to as the yield value. While not wishing to be bound by any theory, it is believed that the increased duration of activity of the compositions of the present invention is related, in part, to the yield value. The compositions of the present invention exhibit a unique response to shear stress. When the yield value is exceeded, the gel structure is altered temporarily, allowing the gel to flow. In the eye, this mechanism is partially attributable to the blinking eyelid. When the stress is removed (eyelid at rest), the structure of the gel is partially re-established. Other factors which explain the duration of the formulations of the present invention are related to ionic interactions, and a release mechanism which is explained by a dynamic equilibrium involving normal tear production and the displacement of basic active cations by cations present in tears. This mechanism is mentioned again, below.

Suitable polymers useful in the present invention are carboxyl vinyl polymers. Preferred polymers of this class include the so called Carbomers, available under the trade name Carbopol from the B. F. Goodrich Company; and ethylene maleic anhydride polymeric material, available under the trade name EMA from the Monsanto Company. The known and readily available polymers Carbopol 934 and 940 are specifically preferred. The polymers are used in the aqueous gel compositions at a level up to about 8% by weight; pourable liquid compositions comprise 0.05% to 2.0% by weight polymer.

Basic Active

The preferred basic actives of the present invention are those disclosed above. The most preferred basic actives are betaxolol and timolol. The basic active, in the gel and pourable liquid embodiments, is present at a level of from about 0.01 to 4.0 wt. %; the most preferred range is from 0.10 to 1.0 wt. %.

Ion Exchange Resin

The cationic resin component of the formulations of the present invention provides an additional means of sustained release of the basic active, and appears to be necessary for initial and prolonged comfort. Such resins are characterized as either strongly acidic such as those having sulfonic acid functionality, or weakly acidic cation exchangers such as those having carboxylic acid functionality. The resin must be incorporated as a finely divided powder, that is, 95% of the resulting spheroidal particles must have a diameter less than 20.0 microns. The release of the basic active held by the cation exchange resin and the anionic polymer is achieved when ions naturally present in the tear fluid, principally sodium and potassium, compete with the bound basic active for sites on the polymer vehicle and the ion exchange resin. Thus released, the basic active is presented to the eye surface for transport to the receptor sites.

Any pharmaceutical grade cationic ion exchange resin is suitable for the formulation, and they can be used either in the hydrogen form or in the sodium form. Such resins are readily available, for example, from Rohm & Haas under the "Amberlite" tradename and from Dow Chemical Co. under the "Dowex" tradename.

The ion exchange resin component is present in the formulations of the present invention at a level of from 0.05% to 10.0% by weight. The average particle size diameter of the resin ranges from 1 to 20 microns.

The particle size of the resin is critical, both with respect to mode of action and comfort. Typically the average particle size of the commercially available form of the ion exchange material of choice is about 40 to 150 microns. Such particles are most conveniently reduced to a particle size range of about 1.0 to 25 microns by ball milling according to known techniques.

Other Ingredients

Antimicrobial Preservative:

Ophthalmic products are typically packaged in multidose form. Preservatives are thus required to prevent microbial contamination during use. Suitable preservatives include: benzalkonium chloride, thimerosal, chlorobutanol, methyl paraben, propyl paraben, phenylethyl alcohol, edetate disodium, sorbic acid, Onamer M, or other agents known to those skilled in the art. Typically such preservatives are employed at a level of from 0.001% to 1.0% by weight.

Tonicity Agents:

The tonicity, or osmolality, of the product can be adjusted to either hypotonicity, iotonicity or hypertonicity relative to normal tears by use of conventional materials known to the art. Such tonicity agents, however are limited to nonionic compounds and typically, when employed, range from 0.0% to 10% weight percent in the final product. Nonionic agents representatively include: mannitol, dextrose, glycerine and propyleneglycol; their presence in the final product form, however, is optional.

Formulation

The compositions are formulated in three basic states: 1. gels; 2. pourable liquids; and 3. anhydrous salts:

1. Gels

The cationic exchange resin component is dispersed in water. The basic active component is then added with stirring. The polyanionic polymer component is then added. The resulting product has a viscosity ranging from 1000 to 300,000 cps depending on the anionic polymer concentration. The resulting pH is 3.0 to 8.5, which may be adjusted, if necessary, with HCl or NaOH.

2. Pourable Liquids

The cationic exchange resin component is dispersed in 10 to 50 vol. percent of total water taken in formulation, and then basic active is dispersed and/or dissolved with stirring. The polyanionic polymer, as an aqueous dispersion, is added until the desired pH of the product is obtained. The pH of the product can be adjusted to the desired value by varying basic active/polymer/resin ratio. If desired, final pH of product can be adjusted with addition of either NaOH or HCl. The preferred pH range for ophthalmic formulations is from 3.0 to 8.5. The final product is a dispersion, which may require high energy mixing to break any agglomeration to achieve uniformity. Other formulation ingredients are then added with mixing. The resulting product has a viscosity ranging from 1.0 to 20,000 cps depending on the anionic polymer concentration.

3. Anhydrous Salts

The basic active, the ion exchange resin, and the polyanionic polymer are combined in water and, following mixing, are lyophilized to a powder. Fillers like mannitol and other materials may be added to facilitate the freeze/drying process according to techniques well known to those skilled in the art. The anhydrous salts produced in this manner an then be formulated or reconstituted to aqueous gels and liquids, or can be formulated and shaped as ocular inserts. The lyophilized powder can also be combined with a nonaqueous vehicle to form an ophthalmic ointment.

Such anhydrous salt embodiments of the present invention can also be prepared by extracting the initial aqueous dispersion with an organic solvent such as ethanol, chloroform, benzene, or the like, and evaporating the organic solvent to produce the desired salt complex. The resulting product is substantially equivalent to the above-described lyophilized product.

Utility

The Ophthalmic formulations of the present invention are administered to the eyes as gels, pourable liquids (eye drops), and in the form of ointments and ocular inserts; the latter classifications are formulated from anhydrous salts. All such compositions are formulated to control the release of basic active upon administration to the eye and thereby provide a sustained release effect. Typically such administration is necessary once or twice per day. The precise dosage regiment is left to the routine discretion of the clinician.

The following examples illustrate, but do not limited the compositional or method of treatment aspects of the present invention.

EXAMPLE 1

Preparation of Betaxolol Free Base from Betaxolol Hydrochloride

Betaxolol Hydrochloride is disclosed in U.S. Pat. No. 4,252,984, and is commercially available.

Betaxolol Hydrochloride (0.88 moles) is dissolved in water and the solution is chilled in an ice-bath. To this solution is added a solution of sodium hydroxide (0.97 moles) in water portionwise to make the mixture basic while it is stirred vigorously. At this point the pH of the mixture is approximately 9.6. The resulting white solid is collected by filtration and washed with a large volume of water.

After press/drying in the filter funnel, the semi-dry solid is resuspended in a large volume of water and stirred for 1-2 hours. The white solid is collected by filtration and washed with a large volume of water to afford salt-free Betaxolol free base, which is dried in vacuo.

EXAMPLE 2

| Example 2 | Product Composition | | |
|---|---|---|---|
| | A (wt %) | B (wt %) | C (wt %) |
| Betaxolol | 0.50 | 0.25 | 1.0 |
| CARBOPOL-934 P (Carbomer) | 0.25 | 0.15 | 0.35 |
| Sodium Poly(Styrene-Divinyl Benzene) Sulfonate | 0.25 | 0.125 | 0.50 |
| Benzalkonium Chloride | 0.01 | 0.01 | 0.01 |
| Mannitol | 5.0 | 5.0 | 5.0 |
| Water | To Make 100% | | |

Procedure

Finely divided Amberlite IRP-69 resin, a sodium poly(styrenedivinyl benzene) sulfonate, and the betaxolol are mixed in 50% of the total water volume component to form a uniform dispersion. The Carbopol-934P is added slowly as an aqueous dispersion. The mixture is homogenized at high speed. The other ingredients are added as aqueous solutions. The final volume is made on addition of water. The resultant products, A, B and C, are white uniform suspensions.

EXAMPLE 3

| Example 3 | Product Composition | | |
|---|---|---|---|
| | A (wt %) | B (wt %) | C (wt %) |
| Betaxolol Base | 0.50 | 0.25 | 1.0 |
| Poly(Styrene-Divinyl Benzene) Sulfonic acid | 0.25 | 0.125 | 0.5 |
| Carbopol-934P | 0.20 | 0.1 | 0.35 |
| Benzalkonium Chloride | 0.01 | 0.01 | 0.01 |
| Mannitol | 5.0 | 5.0 | 5.0 |
| Water | To Make 100% | | |

Procedure

The solutions A, B and C of Example 3 are prepared following the procedure of Example 2. The resulting products are white to off-white uniform suspensions with pH between 5.5 to 6.5.

Following the procedure of Examples 2 and 3, substantially equivalent results are obtained when the betaxolol component is replaced by an equivalent amount of timolol, or by any of the previously identified beta blockers and other basic actives, respectively.

The invention has been described herein with reference to certain preferred embodiments. However, as obvious variations thereon will become apparent to those skilled in the art, the invention it not to be considered as limited thereto.

What is claimed is:

1. A sustained release ophthalmic pharmaceutical composition in the form of an aqueous gel, a pourable aqueous dispersion, or anhydrous salt, for controlling and lowering intraocular pressure comprising:
    a therapeutically effective amount of betaxolol;
    an amount of an anionic mucomimetic polymer having carboxylic acid functional groups which comprise from 2 to 7 carbon atoms per functional group and a molecular weight of from 50,000 to 6 million such that the composition in the form of an aqueous gel or pourable aqueous dispersion has a viscosity of about 1 to about 20,000 cps.; and sodium poly(styrenedivinylbenzene) sulfonic acid at a concentration of from about 0.05% to 10.0% by weight, the composition having a pH of from about 3.0 to 8.5.

2. The composition according to claim 1 wherein the composition is an aqueous dispersion.

3. A composition according to claim 1 wherein the betaxolol is present at a concentration of from about 0.01 to 4.0 wt.%.

4. A composition according to claim 1 wherein the anionic mucomimetic polymer comprises carbomer.

5. A composition according to claim 1 wherein the betaxolol is present at a concentration of about 0.25 wt.%, the anionic mucomimetic polymer is carbomer present at a concentration of about 0.20 wt.%, and the sulfonic acid is present at a concentration of about 0.25 wt.%.

6. The composition of claim 1 wherein the particulate cation exchange resin is in the form of a finely divided powder, said powder consisting of spheroidal particles.

7. A method of treatment for controlling and lowering intraocular pressure which comprises administering topically to the affected eye a pharmaceutical composition which includes:
a therapeutically effective amount of betaxolol;
an amount of an anionic mucomimetic polymer having carboxylic acid functional groups which comprise from 2 to 7 carbon atoms per functional group and a molecular weight of from 50,000 to 6 million such that the composition in the form of an aqueous gel or pourable aqueous dispersion has a viscosity of about 1 to about 20,000 cps.; and sodium poly(styrene-divinylbenzene) sulfonic acid at a concentration of from about 0.05% to 10.0% by weight, the composition having a pH of from about 3.0 to 8.5.

8. The method according to claim 7 wherein the composition is an aqueous dispersion.

9. A method according to claim 7 wherein the betaxolol is present at a concentration of from about 0.01 to 4.0 wt.%.

10. A method according to claim 7 wherein the anionic mucomimetic polymer comprises carbomer.

11. A method according to claim 7 wherein the betaxolol is present at a concentration of about 0.25 wt.%, the anionic mucomimetic polymer is carbomer present at a concentration of about 0.20 wt.%, and the sodium poly(styrene-divinylbenzene) sulfonic acid is present at a concentration of about 0.25 wt.%.

12. The method of claim 7 wherein the particulate cation exchange resin is in the form of a finely divided powder, said powder consisting of spheroidal particles.

* * * * *